(12) United States Patent
Hoegerle et al.

(10) Patent No.: US 12,376,940 B2
(45) Date of Patent: Aug. 5, 2025

(54) HOLDING DEVICE FOR SURGICAL HANDPIECES

(71) Applicant: Aesculap AG, Tuttlingen (DE)

(72) Inventors: Roland-Alois Hoegerle, Tuttlingen (DE); Ralf Pfister, Trossingen (DE); Simon Miller, Dreisslingen (DE); André Buerk, Villingen-Schwenningen (DE); Martin Machill, Rietheim-Weilheim (DE); Edgar Blust, Koenigsfeld (DE); Manuel Roth, Donaueschingen (DE); Stephanie Auber, Tuttlingen (DE)

(73) Assignee: Aesculap AG, Tuttlingen (DE)

( * ) Notice: Subject to any disclaimer, the term of this patent is extended or adjusted under 35 U.S.C. 154(b) by 918 days.

(21) Appl. No.: 17/426,251

(22) PCT Filed: Jan. 15, 2020

(86) PCT No.: PCT/EP2020/050931
§ 371 (c)(1),
(2) Date: Jul. 28, 2021

(87) PCT Pub. No.: WO2020/156814
PCT Pub. Date: Aug. 6, 2020

(65) Prior Publication Data
US 2022/0104914 A1    Apr. 7, 2022

(30) Foreign Application Priority Data
Jan. 29, 2019    (DE) .................... 10 2019 102 194.4

(51) Int. Cl.
*A61B 90/50* (2016.01)
*A61B 17/16* (2006.01)
*A61B 90/70* (2016.01)

(52) U.S. Cl.
CPC .......... *A61B 90/50* (2016.02); *A61B 17/1622* (2013.01); *A61B 90/70* (2016.02); *A61B 2217/002* (2013.01)

(58) Field of Classification Search
CPC ...................................................... A61B 90/50
See application file for complete search history.

(56) References Cited

U.S. PATENT DOCUMENTS 2,878,895 A    3/1959  Wiley
3,556,669 A    1/1971  Valeska et al.
(Continued)

FOREIGN PATENT DOCUMENTS

CN    102372240 A    3/2012
CN    103429186 A    12/2013
(Continued)

OTHER PUBLICATIONS

Written Opinion received in International Application No. PCT/EP2020/050931 dated Apr. 22, 2020, with translation, 10 pages.
(Continued)

*Primary Examiner* — Kevin Joyner
(74) *Attorney, Agent, or Firm* — Christopher A. Rothe; CM Law

(57) ABSTRACT

A holding device for holding and supporting at least one medical instrument, more specifically a surgical handpiece. The holding device includes a central feedline, at least one line portion of which is connected to the end portion of a central feedline. At least one surgical handpiece can be coupled to the line portion. The holding device also includes a connector portion formed on another end portion of the central feedline. The connector portion can be coupled to a preliminary cleaning unit, more specifically a water/compressed air gun, and a cleaning unit, more specifically a filter unit connected to a rinsing line.

9 Claims, 1 Drawing Sheet

(56) References Cited

U.S. PATENT DOCUMENTS

Figure 1:
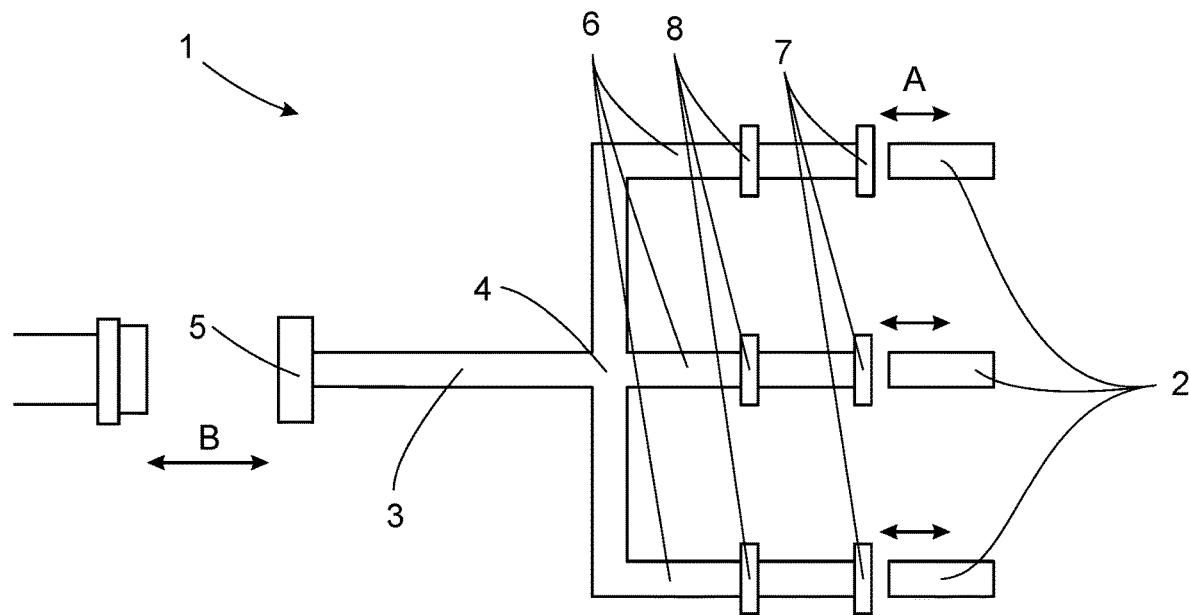

| | | | |
|---|---|---|---|
| 3,811,208 | A | 5/1974 | Vieceli et al. |
| 5,543,119 | A | 8/1996 | Sutter et al. |
| 5,571,488 | A | 11/1996 | Beerstecher et al. |
| 5,723,090 | A | 3/1998 | Beerstecher et al. |
| 2003/0000774 | A1 | 1/2003 | Highley |
| 2005/0236230 | A1* | 10/2005 | Fee .......................... F16N 7/32 184/55.2 |
| 2009/0061384 | A1 | 3/2009 | Thomssen et al. |
| 2013/0312793 | A1 | 11/2013 | Ionidis |
| 2016/0271652 | A1 | 9/2016 | Fukumoto et al. |
| 2017/0007731 | A1* | 1/2017 | Sharma ................. A61B 1/123 |

FOREIGN PATENT DOCUMENTS

| | | |
|---|---|---|
| DE | 4323815 A1 | 1/1995 |
| DE | 102008023458 B | 8/2009 |
| DE | 102010017624 A1 | 12/2011 |
| JP | 2017086346 A | 5/2017 |

OTHER PUBLICATIONS

Office Action received in Japanese Application No. 2021-544260 dated Jul. 14, 2023, with translation, 19 pages.
Office Action received in Chinese Application No. 202080016888.1 dated Feb. 7, 2024, with translation, 12 pages.
Search Report received in German Application No. 10 2019 102 194.4 dated Oct. 14, 2019, with translation, 10 pages.
Search Report received in International Application No. PCT/EP2020/050931 dated Apr. 22, 2020, with translation, 5 pages.
Examination Report received in European Application No. 20701009.1 dated Jun. 7, 2024, with translation, 8 pages.

* cited by examiner

HOLDING DEVICE FOR SURGICAL HANDPIECES

CROSS-REFERENCE TO RELATED APPLICATIONS

This application is the United States national phase entry of International Application No. PCT/EP2020/050931, filed Jan. 15, 2020, and claims the benefit of priority of German Application No. 10 2019 102 194.4, filed Jan. 29, 2019. The contents of International Application No. PCT/EP2020/050931 and German Application No. 10 2019 102 194.4 are incorporated by reference herein in their entireties.

FIELD

The present disclosure relates to a holding device for holding and storing at least one medical instrument, in particular a surgical handpiece, comprising a central feedline, at least one line portion connected to one end of the central feedline on which the at least one medical instrument is arranged, and a connector portion formed at another end of the central feedline.

BACKGROUND

Holding devices are usually used for processing and cleaning surgical handpieces. Surgical handpieces are, for example, burs or shaver handpieces that have a longitudinal channel that cannot be cleaned manually with brushes, since contaminants may be loosened by bristles inside the handpieces, but they cannot be removed completely, leaving behind contamination residues.

The complete processing and cleaning process of the surgical handpieces is divided into manual pre-cleaning, mechanical cleaning and disinfection, a servicing step and a sterilization step. For manual pre-cleaning, the handpiece is placed on a holding device. A water gun is then attached to a connector of the holding device for water and compressed-air guns and the handpiece is flushed with water. The connector for the rinsing hose (the water gun) has to be covered with cellulose or a similar material to prevent the cleaning fluid from flowing out unintentionally. For mechanical cleaning and disinfection, the handpieces are placed on a holding device arranged in a known cleaning and disinfection device and are mechanically rinsed with a cleaning fluid and a disinfection fluid. After mechanical cleaning and disinfection, the residual liquids are removed from the handpiece by manual blowing with the aid of the holding device and the compressed-air gun. After the handpiece has cooled down to ambient temperature, the servicing step is performed with an oil spray. Usually, the handpieces have to be removed, placed individually on an oil spray adapter and sprayed with the oil spray for a certain time, preferably a few seconds. For sterilization, the handpieces are stored on an instrument tray again, since the filter material provided in the holding device is not provided for steam sterilization, as is usually used for sterilizing surgical handpieces.

With conventional holding devices, it may be possible to perform at least the cleaning and servicing steps without time-consuming manual repositioning of the handpieces. DE 10 2010 017 624 A1, for example, discloses a holding device for cleaning and storing surgical handpieces and an instrument tray with the holding device. The holding device has a cleaning fluid connector for introducing a cleaning fluid and a distributor between the fluid connector and at least two handpiece receptacles, onto each of which a handpiece can be placed. A filter device for filtering the cleaning fluid is arranged between the cleaning fluid connector and the handpiece receptacles, however, this filter device is not provided for steam sterilization, so that the holding device can only be used for manual and mechanical cleaning and disinfection.

A further holding device with the possibility of carrying out the cleaning and servicing steps without manual repositioning is disclosed, for example, in U.S. Pat. No. 3,811,208 A. The pneumatic cleaning, disinfection and lubrication device (oiling device) for a tubular dental handpiece comprises a compact and portable reservoir in which a cleaning, disinfection or oiling solution is stored, depending on the application, and a compressed-air source via which compressed air is supplied to the device so that the solution in the reservoir is successively and forcibly converted into an atomized state. Then, the atomized liquid is passed through the attached dental handpiece. However, such a device is not provided for sterilization and storage and is used only for cleaning and servicing the handpieces. Furthermore, the handpieces can only be sprayed individually.

Based on the known prior art, the disadvantage is that during the entire processing and cleaning cycle, the handpieces have to be stored in different storing devices, in particular an instrument tray for sterilization and storage, a holding device for manual and mechanical cleaning and disinfection and an oil spray adapter for servicing and oiling. The fact that the handpieces have to be removed and transferred manually between the various storing devices several times increases the risk of damage or of contamination/pollution of the handpieces.

SUMMARY

It is therefore the object of the invention to avoid or at least reduce the disadvantages of the prior art. In particular, a holding device for surgical handpieces is to be provided which enables cleaning and disinfection, servicing, sterilization and storage of the handpieces during the entire processing cycle with only one holding device, without manual repositioning of the handpieces between the individual processing steps or with the smallest possible number of (manual) processing steps.

This object is solved by a generic device according to a first aspect of the invention in that the connector portion of the holding device for medical instruments according to the invention is configured to be selectively coupled to a pre-cleaning unit, in particular a water/compressed-air gun, and a cleaning unit, in particular a filter unit connected to a rinsing line, and the other end portion of the central feedline, i.e. the end portion of a central feedline fanning out into a number of branch lines holding medical instruments and being close to the connector portion, is configured in the manner of a venturi nozzle.

This has the advantage that the holding device holds the medical instrument, in particular a surgical handpiece, during the entire processing cycle, thus reducing the risk of contamination or pollution after cleaning and servicing. If a puncture spike, which is couplable to an oil unit, in particular a disposable oil reservoir, is preferably arranged at the end portion of the central feedline, which is close to the connector portion, the venturi nozzle causes a vacuum to form in the end portion when the oil flows through the venturi nozzle, i.e. when the oil flows through the end portion, as a result of which oil is sucked out of the oil unit. This in turn has the advantage that even during oiling, which is part of the servicing, the medical instrument or the holding device do not have to be operated manually or the number of individual handling steps during the entire processing process can be reduced. In addition, this configuration eliminates the need for manual blowing out rinsing fluid residues prior to servicing or oiling of the holding device and the at least one surgical handpiece.

In a preferred embodiment, a valve device can be arranged in the at least one line portion of the holding device between the connector portion and the held medical instrument, said valve device being closed in a basic position in which the line portion and the surgical handpiece are uncoupled and opening when the surgical handpiece is coupled to the line portion. If, for example, the surgical handpiece is incorrectly coupled without being aware of it, the risk that rinsing water supplied during cleaning escapes from the incorrectly coupled line portion is reduced compared to the known prior art.

Preferably, the connector portion may be configured as a Luer lock connection.

In a further preferred embodiment, the connector portion can be provided to be couplable to an oil unit, in particular an oil spray or an oil reservoir. The at least one surgical handpiece therefore does not have to be disconnected from the holding device for servicing or oiling, so that both the at least one surgical handpiece and functional parts of the holding device can be oiled simultaneously in one step.

BRIEF DESCRIPTION OF THE DRAWING FIGURES

Figure 2:
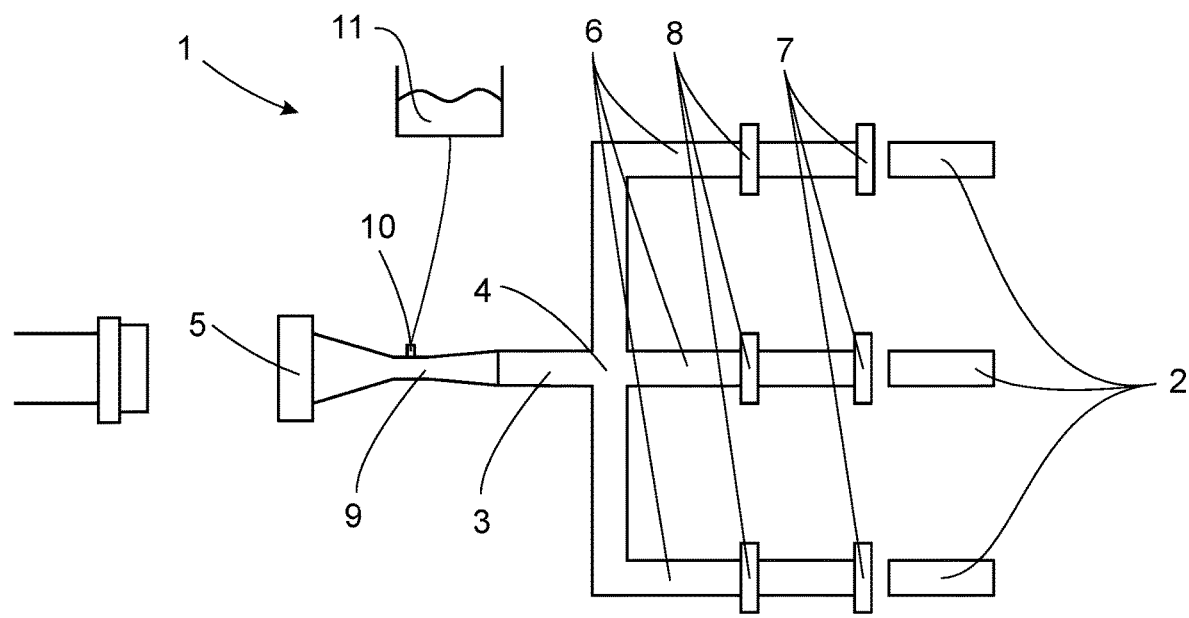

FIG. 1 is a schematic representation of a holding device for holding and storing surgical handpieces according to a first embodiment; and FIG. 2 is a schematic representation of a holding device for holding and storing surgical handpieces according to a modification of the first embodiment.

DETAILED DESCRIPTION

A preferred configuration example of the present disclosure is described hereinafter based on the accompanying figures.

FIG. 1 is a schematic representation of a holding device 1 for holding and storing surgical handpieces 2 during a processing process of the surgical handpieces 2. In the preferred embodiment, the holding device 1 comprises a central feedline 3, which is in fluid connection with a distribution portion 4 at a first end portion and has a connector portion or line coupling 5 at a second end portion.

In the preferred embodiment, the central feedline 3 at the distribution portion 4 divides into preferably three line portions/branch line portions 6, at the end portions/ends of which facing away from the distribution portion 4, the surgical handpieces 2 are arranged so that they are each couplable via a coupling device 7, as indicated in FIG. 1 by the movement arrows A, so that in the coupled state of the connector portion 5 of the holding device 1, a fluid connection is established with the surgical handpieces 2 via the central feedline 3, the distribution portion 4 and the respective line portion 6.

Furthermore, in the preferred embodiment, a respective valve device 8 is arranged at/in each of the (three) line portions 6, which in a closed state separates the aforementioned fluid connection between the connector portion 5 and the respective handpiece 2, and in an open state allows a fluid flow from the connector portion 5 to the respective handpiece 2. The valve device 8 is configured such that the valve device 8 is in the opened state when the surgical handpiece 2 is coupled to the respective coupling device 7, and is in the closed state when no handpiece 2 is coupled to the respective coupling device 7.

According to the present disclosure, the connector portion 5 is configured (quasi as a universal connector) to be couplable to different units, e.g. a filter unit, a compressed-air/water gun and an oil spray or an oil reservoir, as indicated by the movement arrow B in FIG. 1. In the preferred embodiment, the connector portion 5 is configured as a so-called Luer lock connection, which establishes the fluid connection between the coupled unit and the connector portion 5 in a force-fit manner. The respective coupled units as well as their function and interaction with the holding device 1 will become clear in the following description of an exemplary processing process of the surgical handpieces 2.

For processing the surgical handpieces 2, they are first coupled to the holding device 1 (mechanically and fluidically) via the coupling devices 7. In the preferred embodiment, as described above, up to three handpieces 2 can be coupled and processed simultaneously, wherein more branch lines can also be provided. Next, the water gun can optionally be connected to the connector portion 5 so that a first manual pre-cleaning of the holding device 1 and of the surgical handpieces 2 can be performed by injecting water.

In the connector, a rinsing line of a cleaning and disinfection device, via which a rinsing fluid is supplied to the holding device 1, is coupled to the connector portion 5 for mechanical cleaning and disinfection. A connector end portion of the rinsing line has the filter unit described above, which prevents contamination particles from entering the holding device 1 with the rinsing fluid during mechanical cleaning of the holding device 1 and the surgical handpieces 2. After rinsing the holding device 1 and the handpieces 2 with the rinsing fluid, a disinfection fluid is supplied via the rinsing line.

Any liquid residues possibly remaining in the holding device 1 and in the surgical handpieces 2 have to be blown out before oiling. For this purpose, the holding device 1 is decoupled from the cleaning and disinfection device and the compressed-air gun is coupled to the connector portion 5 so that air blown in with the compressed-air gun can remove the liquid residues.

After the surgical handpieces 2 have cooled down to ambient temperature, oil contained in a container is atomized and fed to the holding device 1 and the handpieces 2 for servicing or oiling the handpieces 2 and the holding device 1. Analogously to the filter unit used for manual pre-cleaning, the compressed-air gun is coupled to the connector portion 5. A distal end of the line connected to the compressed-air gun is now connected to an oil reservoir, so that when the compressed-air gun is operated, oil is sucked in from the reservoir, is forcibly atomized and a resulting air-oil mixture is fed to the holding device 1 and the surgical handpieces 2.

In the preferred embodiment, the oil is stored in an oil reservoir and the air-oil mixture is injected into the holding device 1 via the compressed-air gun. Alternatively, an oil spray can be used for servicing or oiling. In this case, an injection portion of the oil spray is coupled directly to the connector portion 5 of the holding device 1 so that the air-oil mixture formed when the oil is injected is fed to the holding device 1.

After the servicing or oiling, the surgical handpieces 2 are sterilized in a conventional sterilizer. In the preferred configuration example, the holding device 1 is configured such that it can be placed in a sieve basket during sterilization and can be stored in the sieve basket after sterilization, which improves handling.

In the preferred embodiment, the connector portion 5 is adapted to be couplable to a filter unit, a compressed-air/water gun, and an oil spray or oil reservoir. As shown in FIG. 2, in a modification of the preferred embodiment, a nozzle portion 9 may be formed at the end portion of the central feedline 3 facing the connector portion. This nozzle portion 9 is thereby preferably designed in the form of a venturi nozzle, so that a cross-section decreases progressively in the direction of the fluid flow. At a point with a relatively small cross-section, a puncture spike 10 is additionally formed in a branching manner, onto which a disposable oil reservoir can be placed for oiling and which pierces a flexible seal of the disposable oil reservoir and establishes a fluid connection between the reservoir and the nozzle portion 9 of the central feedline 3.

For oiling, the compressed-air gun can now be coupled to the connector portion 5 so that a vacuum is created in the nozzle portion 9 when the compressed-air gun is operated. This sucks the oil into the nozzle portion 9, where it is then forcibly atomized so that an air-oil mixture is formed, which is used to oil the holding device 1 and the surgical handpieces 2. The oiling continues until the disposable oil reservoir is emptied.

If the holding device 1 has the nozzle portion 9 according to the modification of the preferred embodiment, the liquid that may possibly remain in the holding device 1 and the handpieces 2 does not have to be blown out manually by the compressed-air gun after the mechanical cleaning and disinfection described above. Blowing out takes place integrally during the oiling of the holding device 1 or respectively of the handpieces 2.

The invention claimed is:

1. A holding device for holding and storing at least one medical instrument during a processing and cleaning process, the holding device comprising:
   a central feedline;
   at least one line portion connected to a first end portion of the central feedline, at a free end of which a coupling device is arranged for coupling to the at least one medical instrument; and
   a connector portion formed or arranged at a second end portion of the central feedline,
   the connector portion being couplable to a pre-cleaning unit and a cleaning unit,
   the second end portion of the central feedline comprising a venturi nozzle comprising a flow passage having a first portion with a first cross-section and a second portion with a second cross-section, wherein the first cross-section is greater than the second cross-section, and the flow passage reduces in size from the first cross-section to the second cross-section in a direction of fluid flow away from the connector portion, and an oil connector is formed at the second portion in a branching manner, wherein the oil connector is couplable to receive oil from an oil reservoir,
   the at least one line portion comprising a valve device arranged in the at least one line portion, the valve device being closed in a basic position in which the at least one line portion and the at least one medical instrument are uncoupled, and the valve device being opened when the at least one medical instrument is coupled to the at least one line portion, and
   wherein the venturi nozzle is configured such that a flow of air passing through the venturi nozzle in the direction of fluid flow generates a vacuum to draw oil from the oil reservoir, when connected to the oil connector, into the venturi nozzle.

2. The holding device according to claim 1, wherein the connector portion is configured as a Luer lock connection.

3. The holding device according to claim 1, wherein at the second end portion of the central feedline a puncture spike is arranged which is couplable to an oil unit.

4. The holding device according to claim 3, wherein the puncture spike is configured to selectively couple to a removable oil reservoir.

5. The holding device according to claim 1, wherein the connector portion is couplable to an oil unit.

6. The holding device according to claim 1, wherein the second cross-section of the flow passage comprises a minimum cross-section of the flow passage.

7. A processing and cleaning system comprising:
   the holding device according to claim 1;
   a pre-cleaning unit configured to be connected to the connector portion of the holding device; and
   an oil reservoir configured to be connected to the oil connector of the holding device.

8. A holding device for holding and storing at least one medical instrument during a processing and cleaning process, the holding device comprising:
   a central feedline;
   at least one line portion connected to a first end portion of the central feedline, at a free end of which a coupling device is arranged for coupling to the at least one medical instrument; and
   a connector portion formed or arranged at a second end portion of the central feedline,
   the connector portion being couplable to a pre-cleaning unit and a cleaning unit,
   the second end portion of the central feedline comprising a venturi nozzle at which an oil connector is formed in a branching manner which is couplable to an oil reservoir, and
   the at least one line portion comprising a valve device arranged in the at least one line portion, the valve device being closed in a basic position in which the at least one line portion and the at least one medical instrument are uncoupled, and the valve device being opened when the at least one medical instrument is coupled to the at least one line portion,
   wherein at the second end portion of the central feedline a puncture spike is arranged which is couplable to an oil unit, and
   the venturi nozzle is configured such that a flow of air passing through the venturi nozzle in a direction of fluid flow generates a vacuum to draw oil from the oil reservoir, when connected to the oil connector, into the venturi nozzle.

9. The holding device according to claim 8, wherein the puncture spike is configured to selectively couple to a removable oil reservoir.

\* \* \* \* \*